United States Patent
Tanaka

(10) Patent No.: US 7,724,361 B2
(45) Date of Patent: *May 25, 2010

(54) APPARATUS AND METHOD OF INSPECTING DEFECTS IN PHOTOMASK AND METHOD OF FABRICATING PHOTOMASK

(75) Inventor: Junichi Tanaka, Kumamoto (JP)

(73) Assignee: Hoya Corporation, Tokyo (JP)

( * ) Notice: Subject to any disclaimer, the term of this patent is extended or adjusted under 35 U.S.C. 154(b) by 106 days.

This patent is subject to a terminal disclaimer.

(21) Appl. No.: 11/293,306

(22) Filed: Dec. 5, 2005

(65) Prior Publication Data

US 2006/0158642 A1      Jul. 20, 2006

(30) Foreign Application Priority Data

Dec. 6, 2004    (JP) ................ P2004-353249

(51) Int. Cl.
*G01N 21/00* (2006.01)
(52) U.S. Cl. .................................. 356/237.4
(58) Field of Classification Search .... 356/237.1–237.5
See application file for complete search history.

(56) References Cited

U.S. PATENT DOCUMENTS 4,886,975 A * 12/1989 Murakami et al. ..... 250/559.41
5,285,259 A * 2/1994 Saitoh ........................ 356/401
5,790,247 A * 8/1998 Henley et al. ............ 356/237.1
6,482,557 B1 * 11/2002 Chen et al. ..................... 430/30
2002/0180986 A1 * 12/2002 Nikoonahad et al. ........ 356/600

FOREIGN PATENT DOCUMENTS

JP      10-300447 A     11/1998
KR      10-0203530 B1    9/1999

OTHER PUBLICATIONS

U.S. Appl. No. 11/094,357, filed Mar. 31, 2005, Masaaki Kobayashi, et al.
U.S. Appl. No. 11/139,970, filed May 31, 2005, Makoto Murai.
U.S. Appl. No. 11/138,765, filed May 27, 2005, Teruaki Yoshida.

* cited by examiner

*Primary Examiner*—Tarifur Chowdhury
*Assistant Examiner*—Tara S Pajoohi
(74) *Attorney, Agent, or Firm*—Sughrue Mion, PLLC

(57) ABSTRACT

A mura-defect inspection apparatus 10 includes: a light source 12 which irradiates light onto a photomask 50 having a repeated pattern that a unit pattern is regularly arranged on a surface 52A of a transparent substrate 52; and a light receiving member 13 which receives reflected light from the photomask to convert it to received light data, wherein an analyzer 14 analyzes the received light data to detect a mura-defect generated in the repeated pattern, wherein the light source 12 irradiates light onto a back side 52B of the transparent substrate in the photomask.

8 Claims, 5 Drawing Sheets

US 7,724,361 B2

APPARATUS AND METHOD OF INSPECTING DEFECTS IN PHOTOMASK AND METHOD OF FABRICATING PHOTOMASK

This application claims foreign priority based on Japanese Patent application No. 2004-353249, filed Dec. 6, 2004, the contents of which is incorporated herein by reference in its entirety.

BACKGROUND OF THE INVENTION

1. Field of the Invention

The present invention relates to an apparatus and a method of inspecting a mura-defect which detect a mura-defect in patterns in a photomask for fabricating an image device, and a method of fabricating a photomask.

2. Description of the Related Art

Conventionally, for a photomask for use in fabricating an image device such as an image pickup device and a display device, mura-defect inspection has been known as one of the inspection items for inspecting the patterns formed on the surface thereof. The mura-defect is an error having different regularities that have been unintentionally generated in patterns regularly arranged, and the defect is generated by some causes during fabrication process steps.

When a mura-defect occurs in patterns in a photomask for use in fabricating an image pickup device and a display device, such a mura-defect is transferred onto the patterns in an image device to cause sensitivity unevenness and display unevenness in the image device, resulting in the performance of the image device being deteriorated.

Further, the mura-defect in patterns of the image device and in patterns of the photomask cannot be detected in pattern inspection for individual patterns in many cases because microdefects are regularly arranged in general. However, when an area is observed as a whole, the defect can be observed differently from the other parts. Therefore, the mura-defect inspection is mainly conducted by visual inspection such as oblique lighting inspection by human eyes.

However, the visual inspection has a problem such that variations are generated in inspection results according to the individual inspectors because visual inspection tends to largely depend on their subjective evaluations. Then, Conventionally, for the image device (for example, a liquid crystal TFT substrate), for example, a mura-defect inspection apparatus described as disclosed in JP 10-300447 is proposed. The mura-defect inspection apparatus according to JP 10-300447 is structured such that light is irradiated onto a substrate formed with patterns on the surface and scattered light from the edge part of the pattern is sensed by a CCD line sensor to detect unevenness.

Another type of a mura-defect inspection apparatus has been also known in which light is irradiated onto a photomask 50 having a repeated pattern where a unit pattern is regularly arranged on a surface 52A of a transparent substrate 52 (FIG. 8) from a light source 62 obliquely downward in a similar way of JP 10-300447, a light receiving member 63 is used for receiving the reflected light from the repeated pattern of the photomask 50 and converts it to received light data, and an analyzer 64 analyzes the received light data to detect a mura-defect generated in the repeated pattern.

In addition, in FIG. 8, a numeral 55 depicts a chip on which the repeated pattern is formed on the surface 52A of the transparent substrate 52 of the photomask 50. Furthermore, over the surface 52A of the transparent substrate 52, a pellicle film 56 is mounted which protects the repeated pattern from dust and dirt with a pellicle frame 57. Moreover, the photomask 50 is placed on a stage 61 as a back side 52B of the transparent substrate 52 in contact with the stage 61.

However, the mura-defect inspection apparatus shown in FIG. 8 raised the following problem which must be taken into the consideration.

First, as shown in FIG. 4(B), the pattern information that a the light receiving member 63 receives for a light 65 includes the pattern information of the scattered light and reflecting at the edge part of the unit pattern in the repeated pattern of the photomask 50. In addition to this, it also receives a light 66 having pattern information that light has passed between unit patterns of the repeated pattern and reflected at a back side 52B of the transparent substrate 52.

Therefore, the analyzer 64 which analyzes received light data from the light receiving member 63 might not detect a mura-defect highly accurately.

Next, as shown in FIG. 5(B), when light is irradiated onto the repeated pattern of the photomask 50 protected by the pellicle film 56 from the light source 62 obliquely downward, an area is generated in the repeated pattern where the light irradiated from the light source 62 is blocked by a pellicle frame 57 and the reflected light cannot be received by the light receiving member 63, and thus a mura-defect might not be detected highly accurately.

Furthermore, as shown in FIG. 6(B), when light from the light source 62 passes through the pellicle film 56, reflects at the edge part of the unit pattern in the repeated pattern, and again passes through the pellicle film 56, the transmittance of the pellicle film 56 affects light intensity to drop to reduce the contrast of received light data at the light receiving member 63, and thus a mura-defect might not be detected highly accurately.

Moreover, as shown in FIG. 7(B), since the stage 61 is in contact with the back side 52B of the transparent substrate 52 and supports the photomask 50, when the transparent substrate 52 has variations in its thickness, the position of the surface 52A formed with the repeated pattern in the transparent substrate 52 is varied with respect to the stage 61. Thus, the focus plane in the light receiving member 63 needs to be adjusted in accordance with the position of the surface 52A of the transparent substrate 52 for each photomask 50.

SUMMARY OF THE INVENTION

The invention has been made in view of said circumstances. An object in the invention is to provide an apparatus and a method of inspecting a mura-defect which can detect a mura-defect highly accurately and a method of fabricating a photomask.

A mura-defect inspection apparatus of the invention according to aspect 1 is a mura-defect inspection apparatus including: a light source which irradiates light onto a test object disposed having a repeated pattern that a unit pattern is regularly arranged on a surface of a transparent substrate, said test object having a repeated pattern on which a unit pattern is regularly arranged; and a light receiving member which receives reflected light or transmitted light from the test object so as to obtain a convert it to received light data, said received light data being analyzed to detect the mura-defect generated in the repeated pattern, wherein the light source irradiates light onto a back side of the transparent substrate on which the test object is disposed.

In the invention according to aspect 1, a mura-defect inspection apparatus of the invention according to aspect 2, wherein a stage on which supporting the test object is placed and supported is in contact with a surface of the transparent substrate in the test object and supports the test object.

In the invention according to aspect 1 or 2, a mura-defect inspection apparatus of the invention according to aspect 3, wherein a pellicle film which covers and protects the repeated pattern is disposed over the surface of the transparent substrate on which the test object is disposed.

In the invention according to any one of aspects 1 to 3, a mura-defect inspection apparatus of the invention according to aspect 4, wherein the test object is a photomask for use in fabricating an image device.

A mura-defect inspection method of the invention according to aspect 5 is a mura-defect inspection method including: irradiating light onto a test object disposed having a repeated pattern that a unit pattern is regularly arranged on a surface of a transparent substrate, said test object having a repeated pattern that a unit pattern is regularly arranged; receiving reflected light or transmitted light from the test object so as to convertobtain a it to received light data; and analyzing the received light data to detect an muraa mura-defect generated in the repeated pattern, wherein light is irradiated onto the test object from a back side of the transparent substrate inon which the test object is disposed.

A fabrication method of fabricating a photomask of the invention according to aspect 6 is a fabrication method of fabricating a photomask in which a photomask having a predetermined light-shielding film pattern on a transparent substrate, the method including: a light-shielding film pattern forming step which formsing a light-shielding film pattern formed of a repeated pattern that which is constituted of a large numbers of unit patterns are regularly arranged formed on the transparent substrate, each unit pattern of said unit patterns having a corresponding repeated pattern;

irradiating light onto a test object disposed on a surface of a transparent substrate, said test object having a repeated pattern that a unit pattern is regularly arranged; receiving reflected light or transmitted light from the test object so as to obtain a received light data; and analyzing the received light data to detect a mura-defect generated in the repeated pattern, wherein light is irradiated onto the test object from a back side of the transparent substrate on which the test object is disposed.

According to the invention of aspect 1, since the light source irradiates light onto the back side of the transparent substrate in the test object, when the light receiving member receives the reflected light from the repeated pattern, the light receiving member receives the reflected light having pattern information that light has scattered and reflected at the edge part of the unit pattern in the repeated pattern, and does not receive light having other pattern information. Therefore, a mura-defect generated in the repeated pattern of the test object can be detected highly accurately.

According to the invention of aspect 2, the stage on which the test object is placed and supported is in contact with the surface of the transparent substrate on which the repeated pattern is formed in the test object, and the stage supports the test object. Thus, even when the transparent substrate has variations in its thickness, the position of the repeated pattern becomes fixed with respect to the stage. Therefore, the focus plane of the light receiving member which receives the reflected light from the repeated pattern can be made fixed.

According to the invention of aspect 3, also when the pellicle film which covers and protects the repeated pattern is disposed over the surface of the transparent substrate in the test object, the light from the light source does not penetrate through the pellicle film. Therefore, the pellicle film does not reduce light intensity, and thus the light receiving member can be prevented from reducing the contrast of received light data as well as a pellicle frame supporting the pellicle film can be prevented from blocking light.

According to the invention of aspect 5 or 6, light is irradiated onto the test object from the backside of the transparent substrate in the test object. Thus, the reflected light having pattern information that light has scattered and reflected at the edge part of the unit pattern in the repeated pattern is received, and the light having other pattern information is not received. Therefore, a mura-defect generated in the repeated pattern of the test object can be detected highly accurately.

DESCRIPTION OF THE PREFERRED EMBODIMENTS

Embodiments of the present invention will be described herein below by reference to the drawings. Unless otherwise specifically defined in the specification, terms have their ordinary meaning as would be understood by those of ordinary skill in the art.

Hereinafter, the best mode for carrying out the invention will be described with reference to the drawings.

Figure 1:
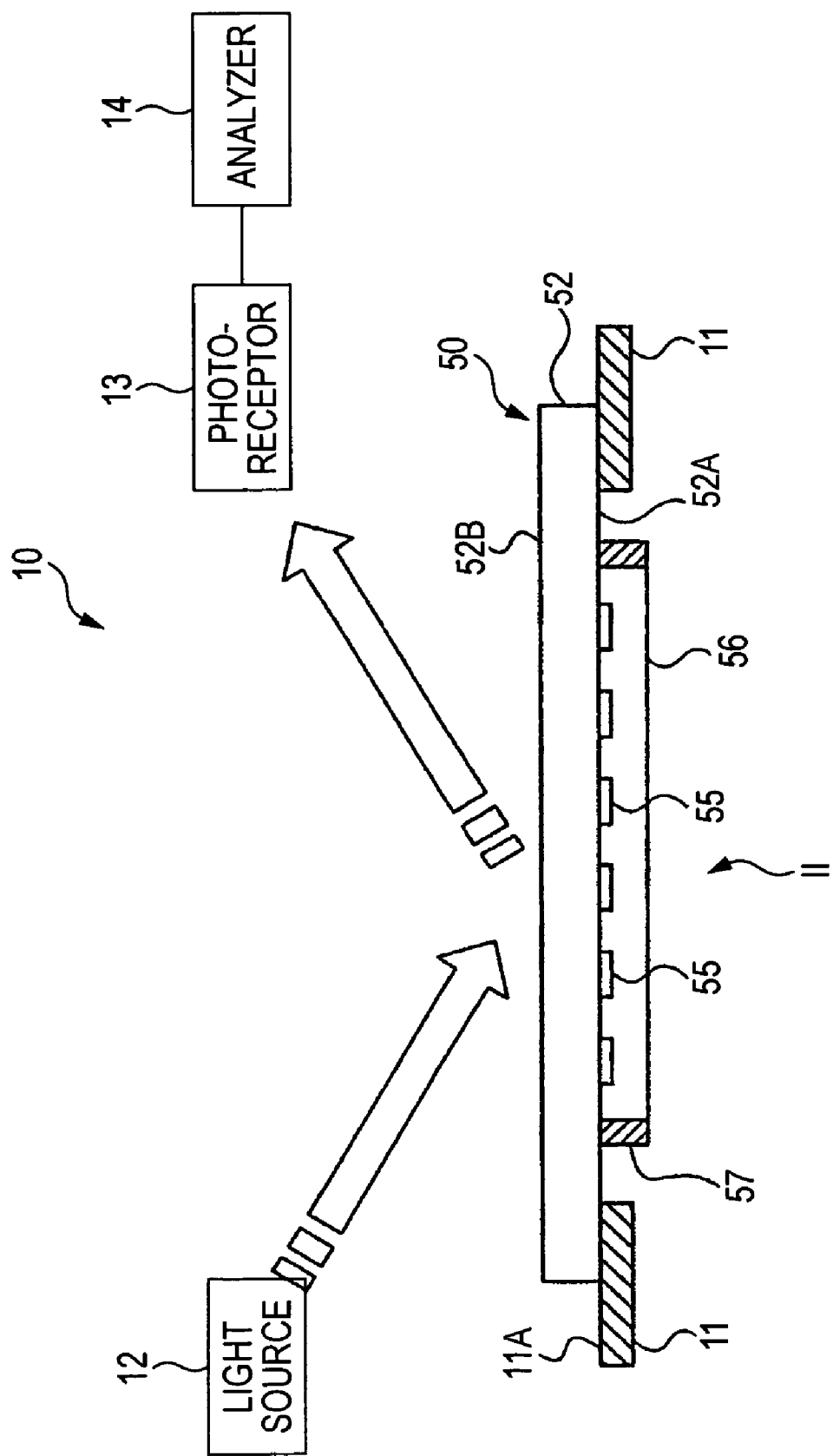
FIG. 1 is a side cross section illustrating an embodiment of a mura-defect inspection apparatus according to the invention.
Figure 2:
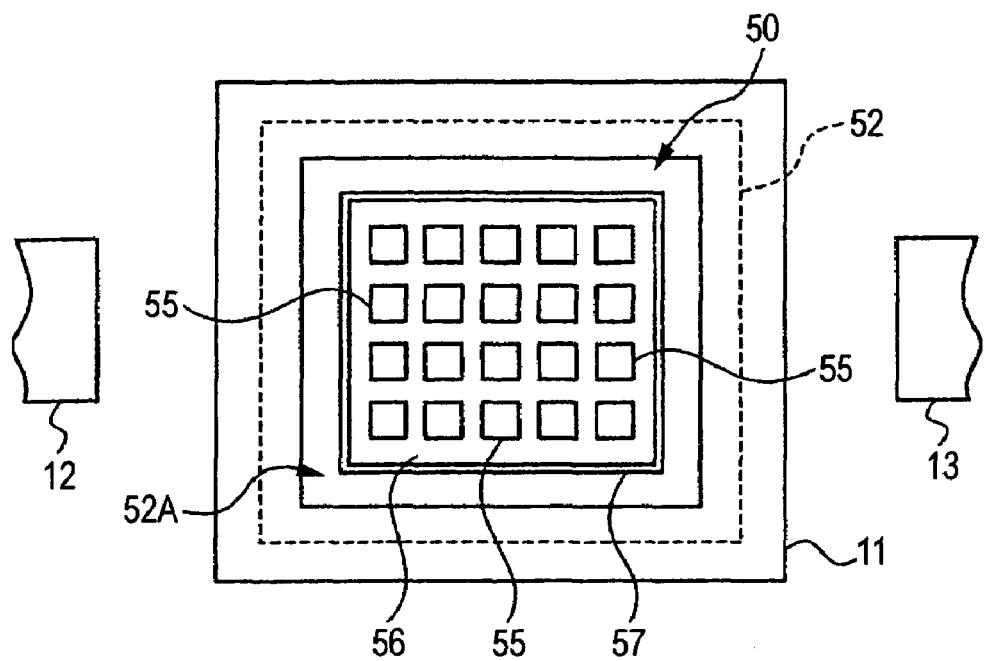
FIG. 2 is a diagram seen from the direction of Arrow II in FIG. 1.

FIG. 1 is a side cross section illustrating an embodiment of a mura-defect inspection apparatus according to the invention. FIG. 2 is a diagram seen from the direction of Arrow II in FIG. 1.

Figure 3:
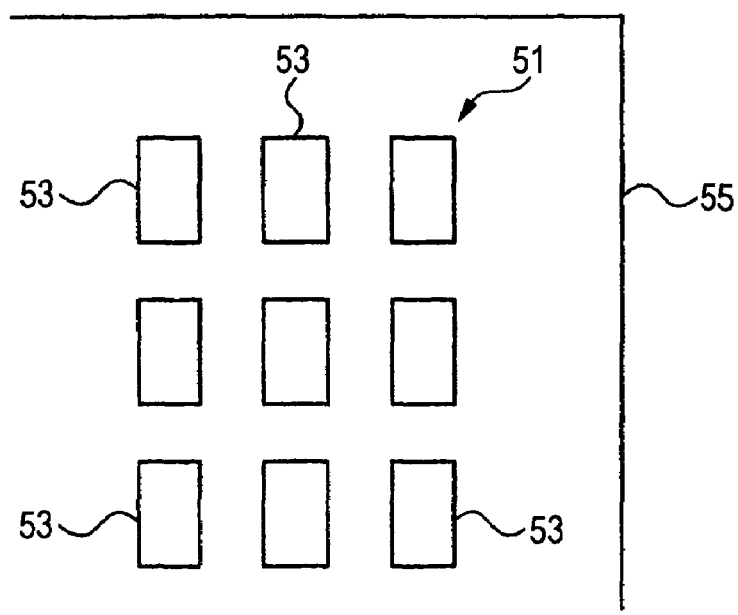
FIG. 3 is a plan view illustrating repeated patterns in the photomask shown in FIG. 2.

A mura-defect inspection apparatus 10 shown in FIGS. 1 and 2 detects a mura-defect generated in a repeated pattern 51 (FIG. 3) formed on the surface of a transparent substrate 52 as a transparent substrate of a photomask 50 that is a test object, which is configured to have a stage 11, a light source 12, a light receiving member 13, and an analyzer 14. The photomask 50 is an exposure mask used for fabricating an image device.

Here, the image device is such a device that a large number of pixel patterns are finally undergo image processing or image display, and an image pickup device and a display device are named. For the image pickup device, solid state image devices such as CCD, CMOS, and VMIS are typical ones. Furthermore, for the display device, a liquid crystal display device, a plasma display device, an EL display device, an LED display device, and a DMD display device are typical ones. Therefore, more specifically, the pixel patterns forming the image pickup plane of the image pickup device are repeated patterns forming a light receiving unit such as CCD and CMOS. Moreover, more specifically, the pixel patterns forming the display plane of the display device are repeated patterns for thin film transistors, a counter substrate, and a color filter of a liquid crystal display panel.

The photomask 50 has a desired repeated pattern 51 (FIG. 3) formed of a light-shielding film pattern formed by partially removing a light-shielding film such as a chromium film on a surface 52A of the transparent substrate 52 such as glass. The repeated pattern 51 is a pattern used for transfer of a large number of pixel patterns for the image device using lithography, which is configured in which a large number of unit patterns 53 are regularly arranged as corresponding to the pixel patterns. Numeral 55 FIGS. 1 and 2 denotes a chip on which the repeated pattern 51 is formed, for example, the pattern is made by about 5×5 on the photomask 50.

To the photomask 50, a pellicle film 56 which covers the repeated pattern 51 to protect the repeated pattern 51 from dust and dirt is further disposed over the surface 52A of the transparent substrate 52. The pellicle film 56 is made of a material having light transmissive properties such as nitro-cellulose, and is placed over the top of a frame-shaped pellicle frame 57. The bottom of the pellicle frame 57 is fixed around the chip 55 on the surface 52A of the transparent substrate 52, and the pellicle film 56 is mounted to the photomask 50.

A fabrication method of the photomask 50 has a light-shielding film pattern forming step which forms a light-shielding film pattern formed of the repeated pattern 51 that a large number of the unit patterns 53 are regularly arranged, and a mura-defect inspecting step which conducts a mura-defect inspection method using the mura-defect inspection apparatus 10 to detect a mura-defect generated in the repeated pattern 51.

In the light-shielding film pattern forming step, the light-shielding film is first formed on the surface 52A of the transparent substrate 52, and a resist film is formed on the light-shielding film. Subsequently, an electron beam or laser beam of a writing unit is irradiated onto the resist film for writing, and a predetermined pattern is exposed. Then, the written part and the non-written part are selectively removed to form a resist pattern. After that, the resist pattern is used as a mask to etch the light-shielding film, and the repeated pattern 51 formed of a large number of the unit patterns 53 (FIG. 3) on the light-shielding film to form a light-shielding film pattern.

In the light-shielding film pattern forming step described above, when the resist film is written by electron beam or laser beam scanning, a seam is generated depending on the beam scan width and beam diameter, and an error caused by writing failure sometimes periodically occurs in the seam in every written unit, causing a mura-defect to occur.

The stage 11 of the mura-defect inspection apparatus 10 shown in FIG. 1 is a stage on which the photomask 50 is placed. As shown in FIG. 2, the stage 11 is a plate in a rectangular frame, for example. A top 11A is in contact with the surface 52A of the transparent substrate 52 in the photomask 50 to place and support the photomask 50 as the back side 52B of the transparent substrate 52 faced above.

As shown in FIG. 1, the light source 12 is disposed obliquely above on one side of the stage 11, which irradiates light onto the back side 52B of the transparent substrate 52 in the photomask 50 from obliquely above. The light from the light source 12 penetrates through the transparent substrate 52 of the photomask 50, and reaches the repeated pattern 51 formed on the surface 52A of the transparent substrate 52.

The light receiving member 13 is disposed obliquely above the other side of the stage 11, which receives the reflected light having reflected from the repeated pattern 51 of the photomask 50, particularly the scattered light having scattered at the edge part of the unit pattern 53 in the repeated pattern 51 at the position obliquely above, and converts it to received light data. For example, for the light receiving member 13, an image pick up sensor such as a CCD line sensor or a CCD area sensor is used. In received light data converted by the light receiving member 13, the regularity of the received light data is disturbed when a mura-defect occurs in the repeated pattern 51 of the photomask 50. Therefore, the analyzer 14 analyzes the received light data to detect a mura-defect.

In the mura-defect inspecting step in the fabrication method of the photomask 50, a mura-defect inspection method using the mura-defect inspection apparatus 10 is conducted to inspect (detect) a mura-defect generated in the repeated pattern 51 of the photomask 50 in which light is irradiated from the light source 12 of the mura-defect inspection apparatus 10 onto the repeated pattern 51 of the photomask 50, the light receiving member 13 receives the scattered light having scattered at the edge part of the unit pattern 53 in the repeated pattern 51, and the analyzer 14 analyzes received light data.

Therefore, according to the embodiment, the following advantages (1) to (4) are exerted.

Figure 4:
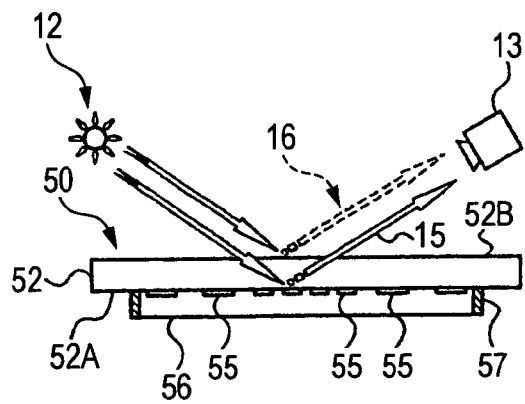
FIGS. 4(A) and 4(B) are the partial side cross sections illustrating mura-defect inspecting conditions by the mura-defect inspection apparatus shown in FIG. 1 along with a comparative example shown in FIG. 8.
Figure 4:
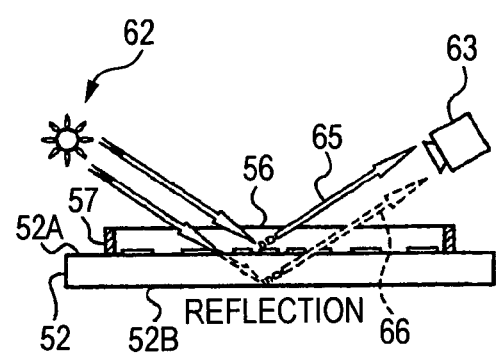

(1) As shown in FIG. 4(A), since the light source 12 irradiates light onto the back side 52B of the transparent substrate 52 in the photomask 50, the light receiving member 13 receives a reflected light 15 having pattern information that light has scattered and reflected at the edge part of the unit pattern 53 in the repeated pattern 51 of the photomask 50, and does not receive light having other pattern information, that is, it does not receive the light 66 having pattern information that light has passed between the unit patterns 53 in the repeated pattern 51 and reflected at the back side 52B of the transparent substrate 52 as shown in FIG. 4(B). In addition, the light receiving member 13 receives a light 16 having reflected at the back side 52B of the transparent substrate 52, but the light 16 does not include pattern information, thus not affecting the detection of a mura-defect. Therefore, the analyzer 14 analyzes the received light data that has been received and converted by the light receiving member 13, and thus a mura-defect generated in the repeated pattern 51 can be detected highly accurately.

Figure 5:
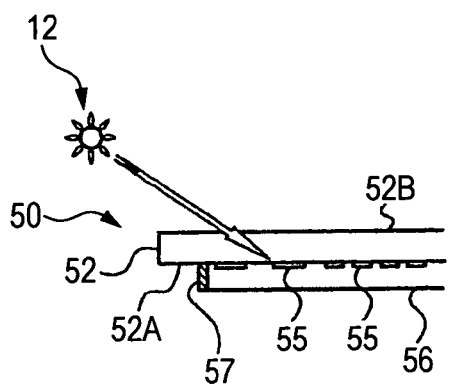
FIGS. 5(A) and 5(B) are the partial side cross sections illustrating mura-defect inspecting conditions by the mura-defect inspection apparatus shown in FIG. 1 along with a comparative example shown in FIG. 8.
Figure 5:
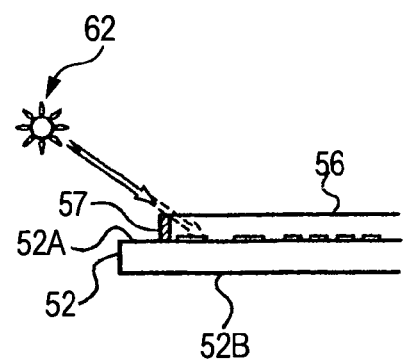

(2) As shown in FIG. 5(A), in the case where the pellicle film 56 which covers and protects the repeated pattern 51 is mounted over the surface 52A of the transparent substrate 52 in the photomask 50 by the pellicle frame 57, when light is irradiated onto the photomask 50 from the light source 12 obliquely downward, the pellicle frame 57 does not block the light from the light source 12, and the light is irradiated onto the entire repeated pattern 51 in the photomask 50. Thus, a mura-defect generated in the repeated pattern 51 can be detected highly accurately.

Figure 6A:
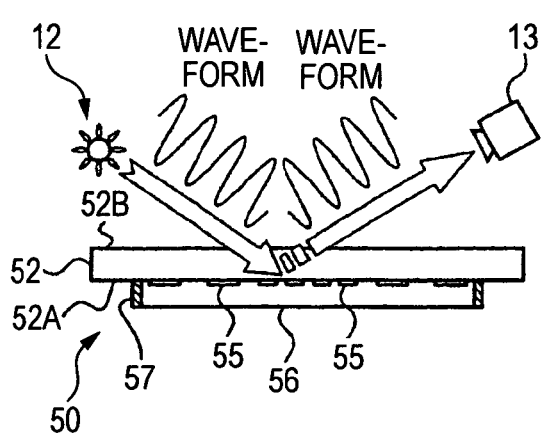
FIGS. 6(A) and 6(B) are the partial side cross sections illustrating mura-defect inspecting conditions by the mura-defect inspection apparatus shown in FIG. 1 along with a comparative example shown in FIG. 8.
Figure 6B:
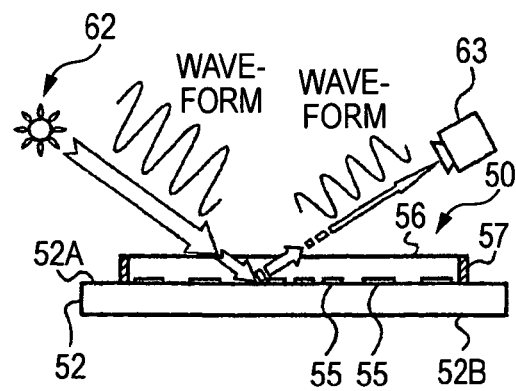

(3) As shown in FIG. 6(A), also in the case where the pellicle film 56 which covers and protects the repeated pattern 51 is mounted over the surface 52A of the transparent substrate 52 in the photomask 50 by the pellicle frame 57, the light from the light source 12 does not penetrate through the pellicle film 56. Consequently, the intensity of the irradiated light from the light source 12 to the repeated pattern 51 and the intensity of the reflected light from the repeated pattern 51 to the light receiving member 13 are not reduced by the pellicle film 56. Therefore, the contrast of received light data that has been received and converted by the light receiving member 13 is not decreased, and thus a mura-defect generated in the repeated pattern 51 can be detected highly accurately.

Figure 7A:
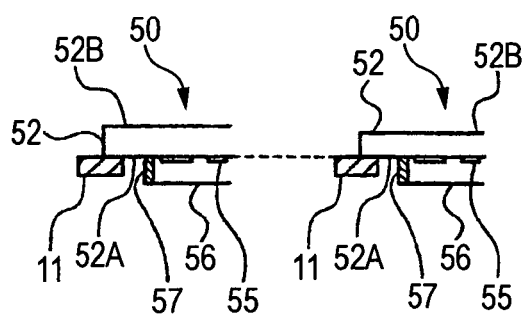
FIGS. 7(A) and 7(B) are the partial side cross sections illustrating mura-defect inspecting conditions by the mura-defect inspection apparatus shown in FIG. 1 along with a comparative example shown in FIG. 8.
Figure 7B:
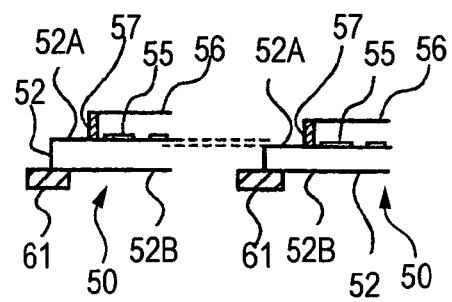
Figure 8:
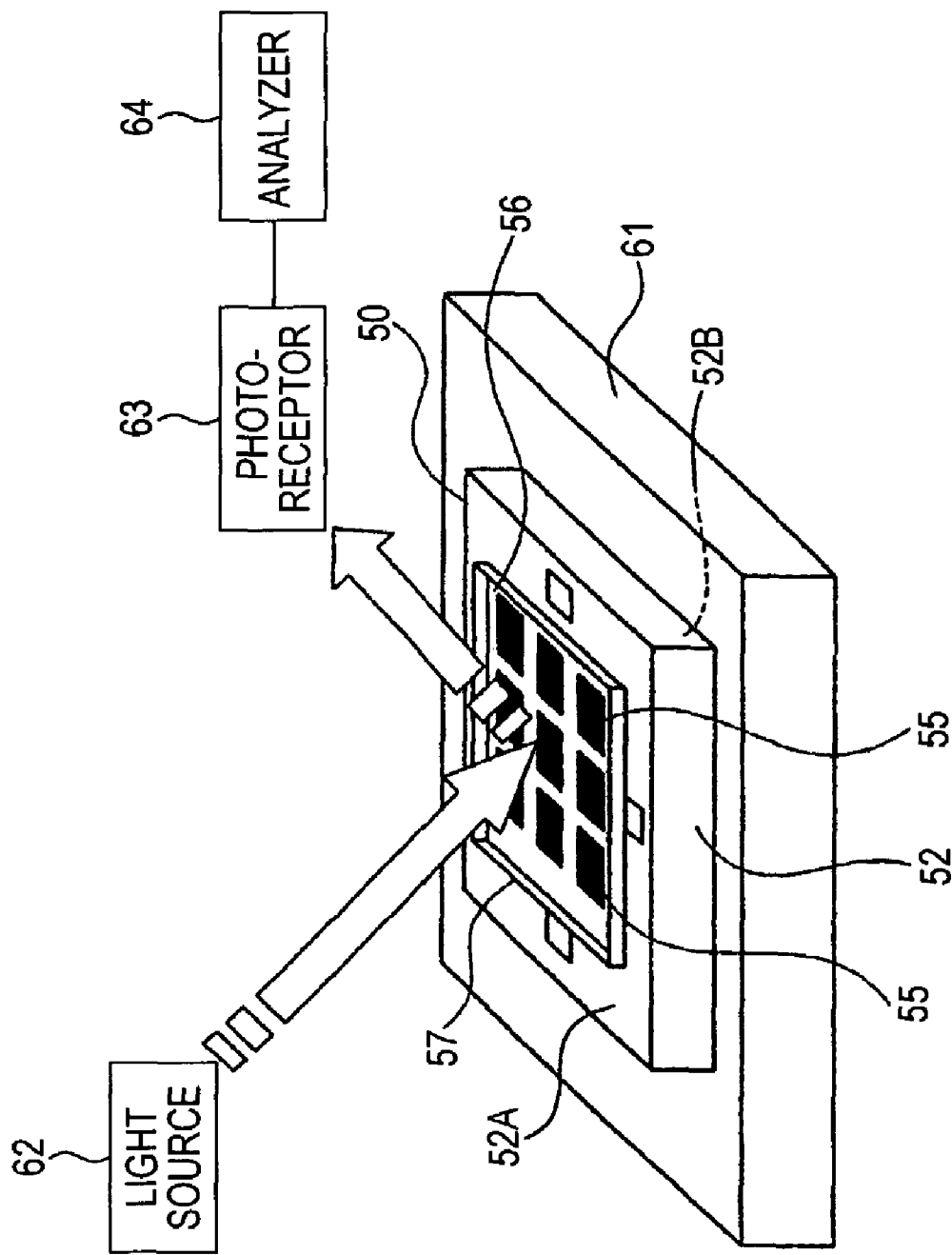
FIG. 8 is a perspective view illustrating a mura-defect inspection apparatus (a comparative example) in FIG. 4(B) to FIG. 7(B).

(4) As shown in FIG. 7(A), the stage 11 on which the photomask 50 is placed and supported is in contact with the surface of 52A of the transparent substrate 52 on which the repeated pattern 51 is formed in the photomask 50, and the stage supports the photomask 50. Therefore, even when the transparent substrate 52 has variations in its thickness, the position of the repeated pattern 51 in the photomask 50 with respect to the stage 11 (that is, the position of the surface 52A in the transparent substrate 52 with respect to the stage 11) becomes fixed. Consequently, since the focus plane of the light receiving member 13 which receives the reflected light from the repeated pattern 51 can be made fixed, the workability of mura-defect inspection work can be improved.

As described above, the invention has been described based on the embodiment, but the invention will not be limited thereto.

For example, the light receiving member 13 in the mura-defect inspection apparatus 10 is described which receives light having scattered at the edge part of the unit pattern 53 in the repeated pattern 51 of the photomask 50, but it may receive transmitted light that passes between the unit patterns 53 in the repeated pattern 51 of the photomask 50, particularly among the transmitted light, it may receive diffracted light diffracted at the edge part of the unit pattern 53.

Furthermore, in the embodiment, the photomask 50 mounted with the pellicle film 56 has been described, but the invention can be adapted to a photomask without the pellicle film 56.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. An apparatus for inspecting a defect occurring in a photomask for fabrication of an image device, the photomask having a transparent substrate and a repeated pattern formed with a light shielding film on a first surface of the transparent substrate and covered with a pellicle film,
    said repeated pattern comprising a plurality of unit patterns arranged in a first regularity and said defect occurring as having a second regularity;
    said apparatus comprising:
        a light source which irradiates light onto the photomask,
        a light receiving member which receives reflected light from the photomask to produce a received light data, said received light data including pattern information of diffracted light generated at the edge part of the unit patterns,
        an analyzer to analyze the received light data to detect the defect occurring in the repeated pattern,
        and a stage for supporting the photomask in a state that the first surface of the photomask is in contact with the stage,
        wherein the light source irradiates the light onto the photomask from a side of a second surface of the transparent substrate, said second surface having no pattern and no pellicle film, and, the analyzer analyzes a disturbance in the regularity in the received light data caused by the defect.

2. The defect inspection apparatus according to claim 1, wherein the light irradiated on the second surface is first received from a side of the transparent substrate nearest to the second surface.

3. A method for defect inspection of a photomask for fabrication of an image device, comprising the steps of;
    irradiating light onto a photomask having a transparent substrate and a repeated pattern formed with a light shielding film on a first surface of the transparent substrate and covered with a pellicle film, said repeated pattern comprising a plurality of unit patterns arranged in a first regularity and said defect occurring as having a second regularity;
    receiving reflected light from the photomask to make a received light data, said received light data including pattern information of diffracted light generated at the edge part of the unit patterns; and
    analyzing the received light data to detect a defect occurring in the repeated pattern,
    wherein the light irradiation is performed onto the photomask from a side of a second surface of the transparent substrate, said second surface having no pattern and no pellicle film, and the analyzing is carried out in detecting a disturbance in the regularity in the received light data caused by the defect.

4. A method for defect inspection according to claim 3, wherein the light irradiated on the second surface is first received from a side of the transparent substrate nearest to the second surface.

5. A method of defect inspection according to claim 3 further comprising supporting the photomask on a stage in a state that the first surface of the photomask is in contact with the stage, prior to said light irradiation.

6. A method of fabricating a photomask for fabrication of an image device, which photomask having a transparent substrate and a repeated pattern of light shielding film formed on a surface of the substrate, the method comprising the steps of:
    forming the repeated pattern of light shielding film, said repeated pattern comprising a plurality of unit patterns arranged in a first regularity, on the first surface of the transparent substrate and covering the repeated pattern with a pellicle film, to make a photomask for inspection;
    irradiating light onto the photomask for inspection;
    receiving reflected light from the photomask for inspection to obtain a received light data; and
    analyzing the received light data to detect a defect occurring as having a second regularity in the repeated pattern, said received light data including pattern information of diffracted light generated at the edge part of the unit patterns;
    wherein the light irradiation is performed onto the photomask from a side of a second surface of the transparent substrate, said second surface having no pattern and no pellicle film, and the analyzing is carried out in detecting a disturbance in the regularity in the received light data caused by the defect.

7. A method of fabricating a photomask according to claim 6, wherein the light irradiated on the second surface is first received from a side of the transparent substrate nearest to the second surface.

8. A method of fabricating a photomask according to claim 6 further comprising supporting the photomask on a stage in a state that the first surface of the photomask is in contact with the stage, prior to said light irradiation.

* * * * *